(12) United States Patent
Jang et al.

(10) Patent No.: US 9,586,979 B2
(45) Date of Patent: Mar. 7, 2017

(54) AMINO-SILYL AMINE COMPOUND, METHOD FOR PREPARING THE SAME AND SILICON-CONTAINING THIN-FILM USING THE SAME

(71) Applicant: DNF CO., LTD., Daejeon (KR)

(72) Inventors: Se Jin Jang, Daegu (KR); Sang-Do Lee, Daejeon (KR); Sung Gi Kim, Daejeon (KR); Byeong-il Yang, Daejeon (KR); Jang Hyeon Seok, Daejeon (KR); Sang Ick Lee, Daejeon (KR); Myong Woon Kim, Daejeon (KR)

(73) Assignee: DNF CO., LTD., Daejeon (KR)

( * ) Notice: Subject to any disclaimer, the term of this patent is extended or adjusted under 35 U.S.C. 154(b) by 0 days.

(21) Appl. No.: 14/896,156

(22) PCT Filed: Jun. 5, 2014

(86) PCT No.: PCT/KR2014/005006
§ 371 (c)(1),
(2) Date: Dec. 4, 2015

(87) PCT Pub. No.: WO2014/196827
PCT Pub. Date: Dec. 11, 2014

(65) Prior Publication Data
US 2016/0122369 A1    May 5, 2016

(30) Foreign Application Priority Data

Jun. 7, 2013  (KR) ........................ 10-2013-0065399
Dec. 19, 2013  (KR) ........................ 10-2013-0159399

(51) Int. Cl.
*C07F 7/02*    (2006.01)
*C07F 7/10*    (2006.01)
(52) U.S. Cl.
CPC ................................... *C07F 7/10* (2013.01)

(58) Field of Classification Search
CPC ............ C07F 7/10; C08L 84/04; C23C 16/06
USPC ........................................................ 556/408
See application file for complete search history.

(56) References Cited

FOREIGN PATENT DOCUMENTS

KR   10-2007-0055898   5/2007
KR   10-2011-0021130   3/2011

OTHER PUBLICATIONS

U. Wannagat et al., Chemical Monthly, vol. 99, No. 4, pp. 1376-1382.*
Wannagat et al., Monatshefte fur Chemie (Chemical Monthly) 1968, 99(4), 1376-1382.*
J. Wannagat et al., Zur Umsetzung yon metallierten (Di)Alkylaminosilylamin en mit Chlorsilanen, Chemical Monthly, vol. 99, No. 4, pp. 1376-1382, 1968.
I. Blaszczyk Lezak et al., "Silicon carbonitride films produced by remote hydrogen microwave plasma CVD using a (dimethylamino) dimethylsilane precursor," Chemical vapor deposition, 2005, vol. 11, pp. 44-52.
International Search Report for corresponding International PCT Application No. PCT/KR2014/005006, dated Sep. 24, 2014.

* cited by examiner

*Primary Examiner* — Fereydoun G Sajjadi
*Assistant Examiner* — Kofi Adzamli
(74) *Attorney, Agent, or Firm* — Hauptman Ham, LLP (57) ABSTRACT

Provided are a novel amino-silyl amine compound, a method for preparing the same, and a silicon-containing thin-film using the same, wherein the amino-silyl amine compound has thermal stability and high volatility and is maintained in a liquid state at room temperature and under a pressure where handling is easy to thereby form a silicon-containing thin-film having high purity and excellent physical and electrical properties by various deposition methods.

6 Claims, 5 Drawing Sheets

AMINO-SILYL AMINE COMPOUND, METHOD FOR PREPARING THE SAME AND SILICON-CONTAINING THIN-FILM USING THE SAME

TECHNICAL FIELD

The present invention relates to a novel amino-silyl amine compound, a method for preparing the same, and a silicon-containing thin-film using the same, and more particularly, to a novel amino-silyl amine compound having thermal stability and high volatility and being maintained in a liquid state at room temperature and under a pressure where handling is easy, a method for preparing the same, and a silicon-containing thin-film using the same.

BACKGROUND ART

A silicon-containing thin-film is manufactured in various shapes, including silicon, silicon oxide, silicon nitride, silicon carbonitride, silicon oxynitride, and the like, by various deposition processes in a semiconductor field, and the application field is wide.

In particular, silicon oxide and silicon nitride function as an insulating film, a diffusion prevention film, a hard mask, an etching stop layer, a seed layer, a spacer, trench isolation, intermetallic dielectric material and a protective layer in manufacturing a device, due to significantly excellent block property and oxidation resistance.

Recently, polycrystalline silicon thin-film has been used to a thin-film transistor (TFT), a solar cell, and the like, and the application field becomes various.

As a representative technology known for manufacturing a silicon-containing thin-film, there are metal organic chemical vapor deposition (MOCVD) forming a film on a surface of a substrate by reacting a silicon precursor in a mixed gas form and a reactive gas, or forming a film by direct reaction on a surface, and atomic layer deposition (ALD) forming a film by physical or chemical adsorption of a silicon precursor in a gas form on a surface of a substrate, followed by sequential introduction of a reactive gas. In addition, various technologies for manufacturing a thin-film such as low pressure chemical vapor deposition (LPCVD) using the method, plasma enhanced chemical vapor deposition (PECVD), plasma enhanced atomic layer deposition (PEALD) using plasma capable of being deposited at a low temperature, and the like, are applied to next-generation semiconductor and a display device manufacturing process, thereby being used to form ultra-fine patterns and deposit ultra-thin-film having uniform nano-sized thickness and excellent properties.

Representative examples of a precursor used in forming a silicon-containing thin-film as described in Korean Patent Laid-Open Publication No. KR 2007-0055898 include silanes, silane chlorides, amino silanes and alkoxysilanes, and more specifically, silane chlorides such as dichlorosilane ($SiH_2Cl_2$) and hexachlorodisilane ($Cl_3SiSiCl_3$) and trisilylamine ($N(SiH_3)_3$)), bis-diethylaminosilane ($H_2Si(N(CH_2CH_3)_2)_2$)) and di-isopropylaminosilane ($H_3SiN(i-C_3H_7)_2$)), and the like, and used in a mass production of a semiconductor and a display.

However, a technology of forming a ultra-fine thin-film having a uniform and thin thickness and excellent electrical properties at a desired low temperature according to miniaturization of devices caused by ultra high integration of the devices, an increase in an aspect ratio, and diversification of device material has been demanded, and thus, high temperature process at 600□ or more, step coverage, etching property, and physical and electrical properties of a thin-film at the time of using the existing silicon precursor are emerging as an issue, and accordingly, excellent novel silicon precursor has been demanded to be developed.

RELATED ART DOCUMENT (Patent Document 1) Korean Patent Laid-Open Publication No. KR 2007-0055898

DISCLOSURE

Technical Problem

An object of the present invention is to provide a novel amino-silyl amine compound.

Another object of the present invention is to provide a novel amino-silyl amine compound which is a precursor compound for thin-film deposition.

Another object of the present invention is to provide a method for preparing an amino-silyl amine compound.

Another object of the present invention is to provide a silicon-containing composition for thin-film deposition containing the amino-silyl amine compound of the present invention, a method for manufacturing a thin-film using the same, and a silicon-containing thin-film manufactured by containing the amino-silyl amine compound of the present invention.

Technical Solution

In one general aspect, the present invention provides a novel amino-silyl amine compound capable of forming a silicon thin-film having excellent cohesion, high deposition rate, and superior physical and electrical properties even at a low temperature.

The novel amino-silyl amine compound of the present invention is represented by the following Chemical Formula 1:

Chemical Formula 1 in Chemical Formula 1, $R^1$ to $R^4$ are each independently hydrogen, halogen, (C1-C7)alkyl, (C2-C7)alkenyl, (C2-C7)alkynyl, (C3-C7)cycloalkyl or (C6-C12)aryl, $R^5$ to $R^8$ are each independently hydrogen, (C1-C7)alkyl, (C2-C7)alkenyl, (C2-C7)alkynyl, (C3-C10)cycloalkyl or (C6-C12)aryl, or substituents adjacent to each other are linked to form 5- to 7-membered alicyclic ring;

the alkyl, alkenyl, alkynyl, cycloalkyl, and aryl of $R^1$ to $R^4$, and the alkyl, alkenyl, alkynyl, cycloalkyl, and aryl of $R^5$ to $R^8$ can further substituted with halogen, (C1-C7)alkyl, (C1-C7)alkoxy, or (C1-C7)aryloxy.

The amino-silyl amine compound of the present invention has high volatility to easily form a thin-film. In addition, due to $Si_3N$ trigonal planar molecular structure having three silicon atoms bonded to central nitrogen atom, the amino-silyl amine compound of the present invention has high thermal stability and low activation energy to thereby have excellent reactivity, and does not produce non-volatile by-product to be capable of easily forming a silicon-containing thin-film having high purity.

In order to provide excellent volatility, in the Chemical Formula 1 above representing the amino-silyl amine compound of the present invention, $R^5$ or $R^6$ is each independently (C2-C7)alkyl, (C2-C7)alkenyl, (C2-C7)alkynyl, (C3-C10)cycloalkyl or (C6-C12)aryl, or both may be lined to form 5- to 7-membered alicyclic ring, and if $R^5$ or $R^6$ is hydrogen or methyl, the compound is solid, whereas if $R^5$ or $R^6$ is (C2-C7), the compound is maintained in a liquid state at room temperature and under atmospheric pressure to have significantly high volatility, thereby being easy to form a thin-film, and more preferably, $R^5$ or $R^6$ is C2-C5.

The amino-silyl amine compound of the present invention is a liquid-state compound at room temperature and under atmospheric pressure to have superior volatility, thereby being easy to form a thin-film.

In addition, due to $Si_3N$ trigonal planar molecular structure having three silicon atoms bonded to central nitrogen atom, the amino-silyl amine compound of the present invention has high thermal stability and low activation energy to thereby have excellent reactivity, and does not produce non-volatile by-product to be capable of easily forming a silicon-containing thin-film having high purity.

In order for the amino-silyl amine compound represented by the Chemical Formula 1 above according to an exemplary embodiment of the present invention to form a thin-film having high thermal stability and reactivity, and high purity, it is preferred that in the Chemical Formula 1 above, $R^1$ to $R^4$ may be each independently hydrogen, halogen, (C1-C5)alkyl, (C2-C5)alkenyl, (C2-C5)alkynyl, (C3-C6)cycloalkyl or (C6-C10)aryl, and $R^5$ to $R^8$ may be each independently hydrogen, (C1-C5)alkyl, (C2-C5)alkenyl, (C2-C5)alkynyl, (C3-C5)cycloalkyl or (C6-C10)aryl.

More preferably, in the Chemical Formula 1 above, $R^1$ to $R^4$ may be each independently hydrogen or (C1-C5)alkyl, and $R^5$ to $R^8$ may be each independently hydrogen or (C1-C5)alkyl.

The Chemical Formula 1 may be selected from the following compounds, but the present invention is not limited thereto:

-continued

-continued

The term: "alkyl", "alkoxy", and other substituents including "alkyl" part described in the present invention may include all linear or branched types. In addition, "aryl" described in the present invention, which is an organic radical derived from aromatic hydrocarbon by removal of one hydrogen, may include single or fused ring system including ring atoms of 4 to 7 in each ring, preferably, 5 or 6, and may include a plurality of aryls linked with a single bond. Specific examples of aryl may include phenyl, naphthyl, biphenyl, anthryl, indenyl, fluorenyl, and the like, but the present invention is not limited thereto. Further, "alkenyl" of the present invention, which is linear or branched hydrocarbon including at least one double bond, may include vinyl, prop-1-en, buta-1,3-diene, and the like, but the present invention is not limited thereto, and "alkynyl" of the present invention may include linear or branched hydrocarbon including at least one triple bond.

The amino-silyl amine compound represented by the Chemical Formula 1 above of the present invention may be preferably a silicon-containing precursor compound for thin-film deposition.

In another general aspect, the present invention provides a method for preparing an amino-silyl amine compound represented by the Chemical Formula 1 above, the method including:

preparing a compound represented by the following Chemical Formula 5 by reacting a compound represented by the following Chemical Formula 3 with a compound represented by the following Chemical Formula 4 in the presence of a base represented by the following Chemical Formula 2 or (C1-C7)alkyllithium; and preparing a compound represented by the following Chemical Formula 1 by reacting the compound represented by the following Chemical Formula 5 with a compound represented by the following Chemical Formula 6:

Chemical Formula 2

Chemical Formula 3

Chemical Formula 4

Chemical Formula 5

Chemical Formula 6 in Chemical Formulas 2 to 6, $R^{11}$ to $R^{13}$ are each independently (C1-C7)alkyl;

$R^1$ to $R^4$ are each independently hydrogen, halogen, (C1-C7)alkyl, (C2-C7)alkenyl, (C2-C7)alkynyl, (C3-C7)cycloalkyl or (C6-C12)aryl;

$R^5$ to $R^8$ are each independently hydrogen, (C1-C7)alkyl, (C2-C7)alkenyl, (C2-C7)alkynyl, (C3-C10)cycloalkyl or (C6-C12)aryl, or substituents adjacent to each other may be linked to form 5- to 7-membered alicyclic ring;

the alkyl, alkenyl, alkynyl, cycloalkyl, and aryl of $R^1$ to $R^4$, and the alkyl, alkenyl, alkynyl, cycloalkyl, and aryl of $R^5$ to $R^8$ may be further substituted with halogen, (C1-C7)alkyl, (C1-C7)alkoxy, or (C1-C7)aryloxy;

M is an alkali metal; and $X^1$ or $X^2$ is halogen.

The compound represented by Chemical Formula 6 may be prepared by reacting (C1-C7)alkylmetal (wherein the metal is an alkali metal) and a compound represented by the following Chemical Formula 7:

Chemical Formula 7 in Chemical Formula 7, $R^7$ or $R^8$ is each independently hydrogen, (C1-C7)alkyl, (C2-C7)alkenyl, (C2-C7)alkynyl, (C3-C10)cycloalkyl or (C6-C12)aryl; and the alkyl, alkenyl, alkynyl, cycloalkyl, and aryl of $R^7$ or $R^8$ may be further substituted with halogen, (C1-C7)alkyl, (C1-C7)alkoxy or (C1-C7)aryloxy.

In another general aspect, the present invention provides a method for preparing an amino-silyl amine compound represented by the Chemical Formula 1 above, the method including:

preparing a compound represented by the following Chemical Formula 8 by reacting the compound represented by the following Chemical Formula 4 with the compound represented by the following Chemical Formula 6; and preparing the compound represented by the Chemical Formula 1 above by reacting the compound represented by the following Chemical Formula 8 with the compound represented by the following Chemical Formula 3 in the presence of (C1-C7)alkyllithium:

Chemical Formula 3

Chemical Formula 4

Chemical Formula 6

Chemical Formula 8 in Chemical Formulas 3, 4, 6, and 8, $R^1$ to $R^4$ are each independently hydrogen, halogen, (C1-C7)alkyl, (C2-C7)alkenyl, (C2-C7)alkynyl, (C3-C7)cycloalkyl or (C6-C12)aryl, $R^5$ to $R^8$ are each independently hydrogen, (C1-C7)alkyl, (C2-C7)alkenyl, (C2-C7)alkynyl, (C3-C10)cycloalkyl or (C6-C12)aryl, or substituents adjacent to each other may be linked to form 5- to 7-membered alicyclic ring;

the alkyl, alkenyl, alkynyl, cycloalkyl, and aryl of $R^1$ to $R^4$, and the alkyl, alkenyl, alkynyl, cycloalkyl, and aryl of $R^5$ to $R^8$ may be further substituted with halogen, (C1-C7)alkyl, (C1-C7)alkoxy, or (C1-C7)aryloxy; and $X^1$ or $X^2$ is halogen.

In another general aspect, the present invention provides a method for preparing an amino-silyl amine compound represented by the Chemical Formula 1 above, the method including:

preparing a compound represented by the following Chemical Formula 5 by reacting the compound represented by the following Chemical Formula 3 with the compound represented by the following Chemical Formula 4 in the presence of a base represented by the following Chemical Formula 2 or (C1-C7)alkyllithium; and preparing a compound represented by the following Chemical Formula 1 by reacting the compound represented by the following Chemical Formula 5 with a compound represented by the following Chemical Formula 7 in the presence of the base represented by the following Chemical Formula 2:

Chemical Formula 2

Chemical Formula 3

Chemical Formula 4

Chemical Formula 5

Chemical Formula 7 in Chemical Formulas 2 to 5 and 7, $R^{11}$ to $R^{13}$ are each independently (C1-C7)alkyl;

$R^1$ to $R^4$ are each independently hydrogen, halogen, (C1-C7)alkyl, (C2-C7)alkenyl, (C2-C7)alkynyl, (C3-C7)cycloalkyl, or (C6-C12)aryl;

$R^5$ to $R^8$ are each independently hydrogen, (C1-C7)alkyl, (C2-C7)alkenyl, (C2-C7)alkynyl, (C3-C10)cycloalkyl or (C6-C12)aryl, or substituents adjacent to each other may be linked to form 5- to 7-membered alicyclic ring;

the alkyl, alkenyl, alkynyl, cycloalkyl, and aryl of $R^1$ to $R^4$, and the alkyl, alkenyl, alkynyl, cycloalkyl, and aryl of $R^5$ to $R^8$ may be further substituted with halogen, (C1-C7)alkyl, (C1-C7)alkoxy, or (C1-C7)aryloxy; and $X^1$ or $X^2$ is halogen.

(C1-C7)alkyl lithium according an exemplary embodiment of the present invention is a compound where lithium is bonded to alkyl having carbon atoms of 1 to 7 for example, methyl lithium, n-butyl lithium, and the like, and preferably, n-butyl lithium.

(C1-C7)alkyl metal according an exemplary embodiment of the present invention is a compound where a metal is bonded to alkyl having carbon atoms of 1 to 7, wherein the metal is an alkali metal, for example, Li, Na, and the like, and preferably, Li.

The method may further include:

preparing a compound represented by the following Chemical Formula 14 by reacting the compound represented by the following Chemical Formula 12 with the compound represented by the following Chemical Formula 13 in the presence of the compound represented by the following Chemical Formula 11; and preparing the compound represented by the Chemical Formula 3 above by reacting the compound represented by the following Chemical Formula 14 with the compound represented by the following Chemical Formula 15:

Chemical Formula 11
$$MX^{11}$$

Chemical Formula 12
$$HN\!-\!(\!Si\!-\!R^{22})_2$$
with $R^{21}$ above Si and $R^{23}$ below Si Chemical Formula 13
$$R^1\!-\!Si\!-\!X^{12}$$
with $R^2$ above Si and $X^{12}$ below Si Chemical Formula 14
$$HN\!-\!(\!Si\!-\!X^{12})_2$$
with $R^2$ above Si and $R^1$ below Si Chemical Formula 15
$$HN(R^5)(R^6)$$

in Chemical Formula 11 to 15,

M is B, Al or Sn;

$R^{21}$ to $R^{23}$ are each independently (C1-C7)alkyl;

$R^1$ and $R^2$ are each independently hydrogen, halogen, (C1-C7)alkyl, (C2-C7)alkenyl, (C2-C7)alkynyl, (C3-C7)cycloalkyl, or (C6-C12)aryl;

$R^5$ and $R^6$ are each independently hydrogen, (C1-C7) alkyl, (C2-C7)alkenyl, (C2-C7)alkynyl, (C3-C10)cycloalkyl or (C6-C12)aryl, or may be linked to form 5- to 7-membered alicyclic ring; and $X^{11}$ and $X^{12}$ are each independently halogen.

The Chemical Formula 11 according to an exemplary embodiment of the present invention is a halogenated metal, wherein the metal is B, Al or Sn, preferably, Al.

The solvent used in the preparing method of the present invention is not limited if a solvent is not reacted with the starting material among general organic solvents, for example, may be at least one kind selected from a group consisting of normal hexane (n-hexane), cyclohexane, normal pentane (pentane), diethyl ether, toluene, tetrahydrofuran (THF), dichloromethane (DCM), and trichloromethane (chloroform).

The reaction temperature in the preparing method of the present invention is not limited if temperature is used in general organic synthesis; however, may be varied depending on the reaction time, the reaction material, and an amount of the starting material, wherein the reaction needs to be finished after confirming that the starting material is completely consumed by NMR, GC, and the like. When the reaction is finished, a solvent may be removed by filtration, followed by simple distillation, under reduced pressure, to thereby separate and refine a desired material by general methods such as fractional distillation, distillation under reduced pressure, and the like.

In another general aspect, the present invention provides a silicon-containing composition for thin-film deposition including the amino-silyl amine compound as described above, and a method for manufacturing a silicon-containing thin-film including the same.

The silicon-containing composition for thin-film deposition may contain the amino-silyl amine compound as a precursor for thin-film deposition, and the amino-silyl amine compound in the composition may have a content within the range recognized by a person skilled in the art in consideration of film forming conditions, or thickness, properties, and the like, of the thin-film.

In another general aspect, the present invention provides a silicon-containing thin-film manufactured by containing the amino-silyl amine compound as described above.

The silicon-containing thin-film of the present invention may be manufactured by general methods, for example, metal organic chemical vapor deposition (MOCVD), atomic layer deposition (ALD), low pressure chemical vapor deposition (LPCVD), plasma enhanced chemical vapor deposition (PECVD), plasma enhanced atomic layer deposition (PEALD), and the like.

The amino-silyl amine compound of the present invention has low activation energy, high reactivity and little non-volatile by-products, such that the silicon-containing thin-film manufactured by using the amino-silyl amine compound as a precursor may have high purity and excellent physical and electrical properties.

Advantageous Effects

The amino-silyl amine compound of the present invention has excellent thermal stability and high reactivity, such that the silicon-containing thin-film manufactured by using the amino-silyl amine compound as a precursor may have high purity and significantly excellent physical and electrical properties.

In addition, the amino-silyl amine compound of the present invention may have high content of silicon and be maintained in a liquid state at room temperature and under atmospheric pressure to thereby be easily stored and handled and have high volatility to be rapidly and easily deposited, and it is possible to deposit a thin-film having excellent cohesion and step coverage.

DESCRIPTION OF DRAWINGS

The above and other objects, features and advantages of the present invention will become apparent from the following description of preferred embodiments given in conjunction with the accompanying drawings, in which.

BEST MODE

Hereinafter, the present invention will be described in more detail with reference to the following exemplary embodiments. However, the following exemplary embodiments describe the present invention by way of example only but are not limited thereto.

The following Examples of all compounds were practiced under anhydrous and inert atmosphere using a glovebox or a Schlenk pipe, products were analyzed by $^1$H Nuclear Magnetic Resonance (NMR), thermogravimetric analysis (TGA) and gas chromatography (GC), a thickness of deposited thin-film were measured by Ellipsometer, and components of the films were analyzed by infrared spectroscopy.

Example 1

Synthesis of Diethylamino Dimethyl Disilazane 250 g (1.55 mol) of hexamethyldisilazane ($((CH_3)_3Si)_2NH$) and 10 g (0.075 mol) of aluminum chloride ($AlCl_3$) were put into 2000 mL of flame-dried Schlenk flask under anhydrous and inert atmosphere while stirring, 499.80 g (3.87 mol) of dichloro dimethylsilane (($CH_3)_2SiCl_2$) was slowly added thereto while maintaining temperature of 25° C., and a temperature of the reaction solution was slowly raised to 40° C. The mixed reaction solution was stirred for 3 hours and the produced chlorotrimethylsilane (($CH_3)_3SiCl$) and the excessively added dichloro dimethylsilane (($CH_3)_2SiCl_2$) were removed therefrom by simple distillation or distillation under reduced pressure. The recovered chloro dimethyl disilazane ((($CH_3)_2SiCl)_2NH$)) solution was stirred and then 475.45 g (6.5 mol) of diethylamine (($CH_3CH_2)_2NH$) was slowly added thereto while maintaining temperature of −15° C. After the addition was completed, a temperature of the reaction solution was slowly raised to room temperature, and the reaction solution was stirred at room temperature for 6 hours. After the white solid obtained by filtration was removed to obtain filtrate, solvent was removed from the filtrate under reduced pressure, and 319.90 g (1.16 mol) of diethylamino dimethyl disilazane (($CH_3)_2SiN(CH_2CH_3)_2)_2NH$) was obtained by reduced pressure distillation with a yield of 75%.

$^1$H NMR (in $C_6D_6$) δ 0.14 (s, 12H, $HNSi(CH_3)_2N$), 0.97 (t, 12H, $Si(NCH_2CH_3)_2$), 3.42 (q, 8H, $Si(NCH_2CH_3)_2$), Boiling Point 238° C.

Example 2

Synthesis of Bis-Diethylamino Dimethylsilyl Trimethylsilyl Amine 180 g (0.65 mol) of diethylamino dimethyl disilazane (($CH_3)_2SiN(CH_2CH_3)_2)_2NH$) synthesized by Example 1 above and 200 ml of n-hexane organic solvent were added to 2000 mL of a flame-dried flask under anhydrous and inert atmosphere while stirring, and 202.16 g (0.65 mol) of 2.29M normal butyl lithium (n-$C_4H_9Li$).hexane ($C_6H_{14}$) solution was slowly added while maintaining a temperature of −15° C. After the addition was completed, a temperature of the reaction solution was slowly raised to room temperature, and the reaction solution was stirred for 12 hours and 200 ml of tetrahydrofuran ($O(C_2H_2)_2$) was added thereto. 70.94 g (0.65 mol) of chlorotrimethylsilane ($ClSi(CH_3)_3$)) was slowly added to the reaction solution while maintaining a temperature of −20° C. After the addition was completed, a temperature of the reaction solution was slowly raised to 65° C. and the reaction solution was stirred for 12 hours while maintaining the temperature. After the white solid obtained by filtration was removed to obtain filtrate, solvent was removed from the filtrate under reduced pressure, and 159 g (0.46 mol) of bis-diethylaminosilyl trimethylsilyl amine (($CH_3)_3SiN(Si(CH_3)_2N(CH_2CH_3)_2)_2$) was obtained by reduced pressure distillation with a yield of 70%.

$^1$H NMR (in $C_6D_6$) δ 0.30 (s, 12H, $NSi(CH_3)_2N$), 0.32 (s, 9H, $Si(CH_3)_3$), 0.99 (t, 12H, $Si(NCH_2CH_3)_2$) 2.82 (q, 8H, $Si(NCH_2CH_3)_2$); Boiling Point 279° C.; GC Analysis Result >99.85%.

Example 3

Synthesis of Tris-Diethylamino Dimethylsilyl Amine 180 g (0.65 mol) of diethylamino dimethyl disilazane (($CH_3)_2SiN(CH_2CH_3)_2)_2NH$) synthesized by Example 1 above and 200 ml of n-hexane organic solvent were added to 2000 mL of a flame-dried flask under anhydrous and inert atmosphere while stirring, and 202.16 g (0.65 mol) of 2.29M normal butyl lithium (n-$C_4H_9Li$).hexane ($C_6H_{14}$) solution was slowly added while maintaining a temperature of −15° C. After the addition was completed, a temperature of the reaction solution was slowly raised to room temperature, and the reaction solution was stirred for 12 hours and 200 ml of tetrahydrofuran ($O(C_2H_2)_2$) was added thereto. 108.25 g (0.65 mol) of chloro-dimethyl diethylamino silane synthesized by reacting dichloro dimethylsilane ($Cl_2Si(CH_3)_2$) and 2 equivalents of dimethylamine in a quantitative scheme was slowly added to the reaction solution while maintaining a temperature of −20° C. After the addition was completed, a temperature of the reaction solution was slowly raised to 65° C. and the reaction solution was stirred for 12 hours while maintaining the temperature. After the reaction was completed, the reaction mixture was filtrated and the produced white solid was removed from the reaction mixture to obtain a filtrate. Solvent of the filtrate was removed under reduced pressure, and 119.00 g (0.29 mol) of tris-diethylaminosilyl amine ($N(Si(CH_3)_2N(CH_2CH_3)_2)_3$) was obtained by reduced pressure distillation with a yield of 45%.

$^1$H NMR (in $C_6D_6$) δ 0.37 (s, 18H, $NSi(CH_3)_2N$), 1.02 (t, 18H, $Si(NCH_2CH_3)_2$), 2.86 (q, 12H, $Si(NCH_2CH_3)_2$); Boiling Point 311° C.; GC Analysis Result >99.27%.

Example 4

Synthesis of Tris-Diethylamino Dimethylsilyl Amine 180 g (0.65 mol) of diethylamino dimethyl disilazane (($CH_3)_2SiN(CH_2CH_3)_2)_2NH$) synthesized by Example 1 above and 200 ml of n-hexane organic solvent were added to 2000 mL of a flame-dried flask under anhydrous and inert atmosphere while stirring, and 202.16 g (0.65 mol) of 2.29M normal butyl lithium (n-$C_4H_9Li$).hexane ($C_6H_{14}$) solution was slowly added while maintaining a temperature of −15° C. After the addition was completed, a temperature of the reaction solution was slowly raised to room temperature, and the reaction solution was stirred for 12 hours and 200 ml of tetrahydrofuran ($O(C_2H_2)_2$) was added thereto. 84.30 g (0.65 mol) of dichloro dimethylsilane was slowly added to the reaction solution while maintaining a temperature of −20° C. After the addition was completed, a temperature of the reaction solution was slowly raised to 65° C. and the reaction solution was stirred for 12 hours while maintaining the temperature. After the reaction mixture was filtrated and the obtained white solid was removed from the reaction mixture to obtain a filtrate, 51.65 g (0.65 mol) of lithium diethylamine salt ($LiN(C_2H_5)_2$) obtained by reacting diethylamine ($HN(C_2H_5)_2$) and 2.29M normal butyl lithium (n-$C_4H_9Li$).hexane ($C_6H_{14}$) solution in a quantitative scheme was slowly added thereto while stirring the filtrate and maintaining a temperature of −20° C. After the addition was completed, a temperature of the reaction solution was slowly raised to 65° C. and the reaction solution was stirred for 12 hours while maintaining the temperature. After the white solid obtained by filtration was removed to obtain filtrate, solvent was removed from the filtrate under reduced pressure, and 171.88 g (0.42 mol) of tris-diethylaminosilyl amine ($N(Si(CH_3)_2N(CH_2CH_3)_2)_3$) was obtained by reduced pressure distillation with a yield of 65%.

$^1$H NMR (in$C_6D_6$) δ 0.37 (s, 18H, HNSi($CH_3$)$_2$N), 1.02 (t, 18H, Si(NC$H_2$C$H_3$)$_2$), 2.86 (q, 12H, Si(NC$H_2$CH$_3$)$_2$); Boiling Point 311° C.; GC Analysis Result >99.27%.

Example 5

Synthesis of Dimethylamino Methyl Disilazane 250 g (1.55 mol) of hexamethyldisilazane ((($CH_3$)$_3$Si)$_2$NH) and 10 g (0.075 mol) of aluminum chloride ($AlCl_3$) were put into 2000 mL of flame-dried Schlenk flask under anhydrous and inert atmosphere while stirring, 713.19 g (3.87 mol) of dichloro dimethylsilane (($CH_3$)$_2$SiCl$_2$) was slowly added thereto while maintaining temperature of 25□, and a temperature of the reaction solution was slowly raised to 40□. The mixed reaction solution was stirred for 3 hours and the produced chlorotrimethylsilane (($CH_3$)$_3$SiCl) and the excessively added dichloro dimethylsilane (($CH_3$)$_2$SiCl$_2$) were removed therefrom by simple distillation or distillation under reduced pressure. The recovered chloro methyl disilazane (($CH_3$SiHCl)$_2$NH)) solution was stirred and then 293.47 g (4.2 mol) of diethylamine (($CH_3$)$_2$NH) was slowly added thereto while maintaining temperature of −15□. After the addition was completed, a temperature of the reaction solution was slowly raised to room temperature, and the reaction solution was stirred at room temperature for 6 hours. The white solid obtained by filtration was removed to obtain filtrate. Solvent of the filtrate was removed under reduced pressure, and 222.54 g (1.16 mol) of dimethylamino methyl disilazane (($CH_3$SiHN($CH_3$)$_2$)$_2$NH) was obtained by reduced pressure distillation with a yield of 75%.

$^1$H-NMR (in$C_6D_6$) δ 0.19 (t, 6H, ((($CH_3$)$_2$N($CH_3$)HSi)$_2$NH), 2.46 (s, 12H, ((($CH_3$)$_2$)$_2$N($CH_3$)HSi)$_2$NH), 4.71 (m, 2H, NSiH).

Example 6

Synthesis of Tris-Dimethylaminomethylsilyl Amine 191.43 g (1.00 mol) of dimethylamino methyl disilazane (($CH_3$SiHN($CH_3$)$_2$)$_2$NH) synthesized by Example 5 above and 200 ml of n-hexane organic solvent were added to 2000 mL of a flame-dried flask under anhydrous and inert atmosphere while stirring, and 303.32 g (1.00 mol) of 2.29M normal butyl lithium (n-$C_4H_9Li$).hexane ($C_6H_{14}$) solution was slowly added while maintaining a temperature of −15□. After the addition was completed, a temperature of the reaction solution was slowly raised to room temperature, and the reaction solution was stirred for 12 hours and 300 ml of tetrahydrofuran ($O(C_2H_2)_2$) was added thereto. 123 g (1.00 mol) of chloro-methyl chloro dimethylamino silane synthesized by reacting dichloro methylsilane ($Cl_2SiHCH_3$) and 2 equivalents of dimethylamine in a quantitative scheme was slowly added to the reaction solution while maintaining a temperature of −20□. After the addition was completed, a temperature of the reaction solution was slowly raised to 65□ and the reaction solution was stirred for 12 hours while maintaining the temperature. After the white solid obtained by filtration of the completely reacted reaction mixture was removed to obtain filtrate, solvent was removed from the filtrate under reduced pressure, and 195.03 g (0.70 mol) of tris-dimethylaminomethylsilyl amine (($CH_3$SiHN($CH_3$)$_2$)$_3$N) was obtained by reduced pressure distillation with a yield of 70%.

$^1$H-NMR (in$C_6D_6$) δ 0.28 (m, 9H, NSiCH$_3$) 2.46 (m, 18H, SiN($CH_3$)$_2$), 4.81 (m, 3H, NSiH); Boiling Point 237□; GC Analysis Result >99.5%.

Example 7

Figure 1:
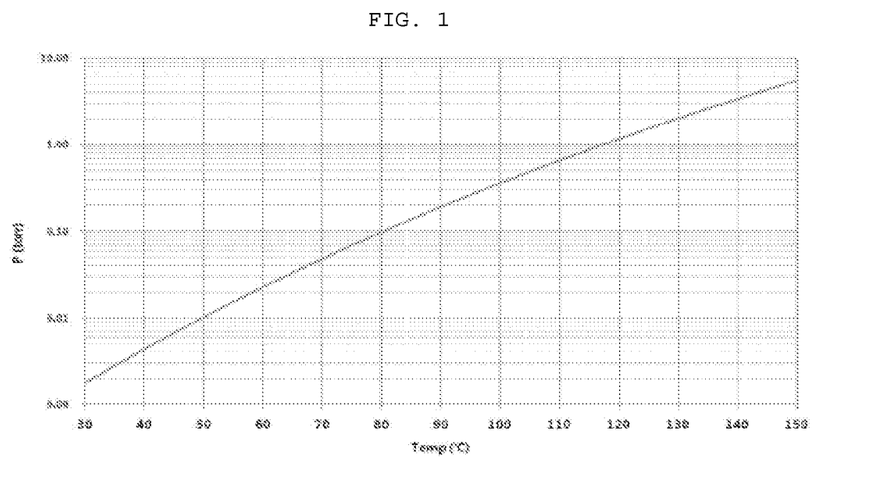
FIG. 1 shows a result obtained by measuring vapor pressure of alkylaminosilane prepared by Example 2.
Figure 2:
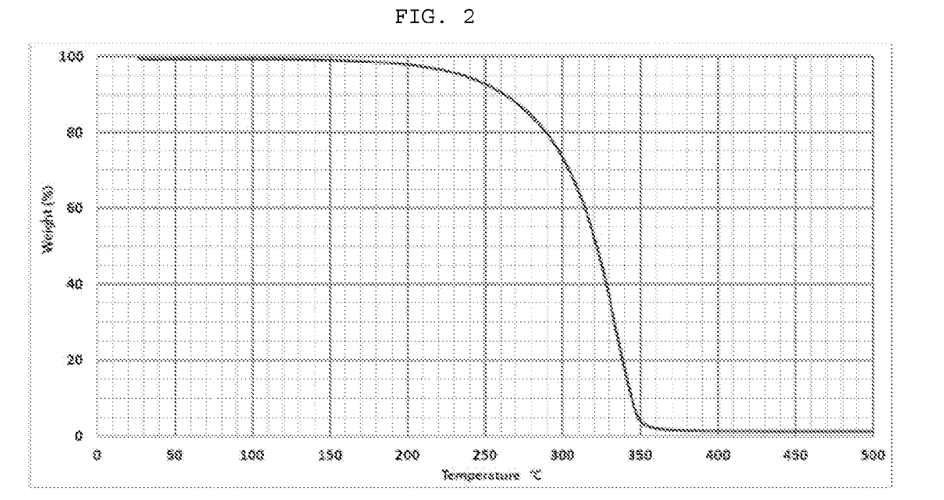
FIG. 2 shows a result obtained by analyzing thermogravimetry of alkylaminosilane prepared by Examples 3 and 4.
Figure 3:
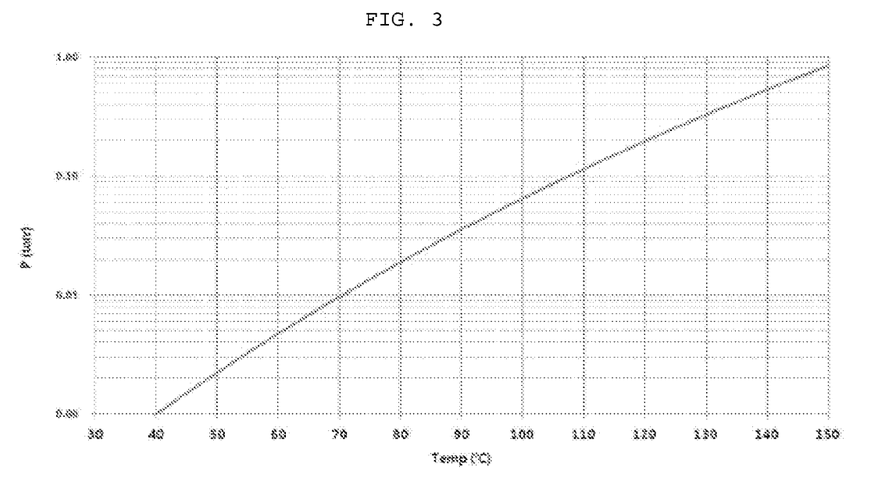
FIG. 3 shows a result obtained by measuring vapor pressure of alkylaminosilane prepared by Examples 3 and 4.
Figure 4:
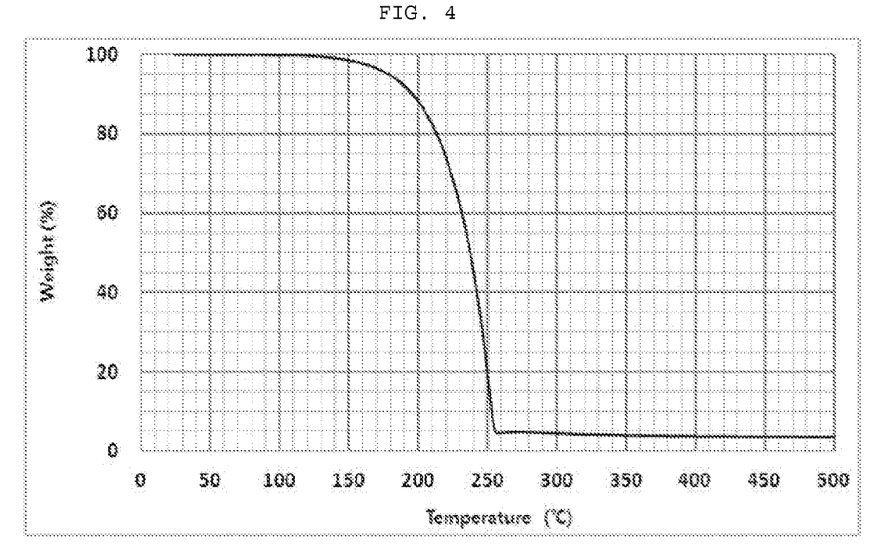
FIG. 4 shows a result obtained by analyzing thermogravimetry of alkylaminosilane prepared by Example 6.
Figure 5:
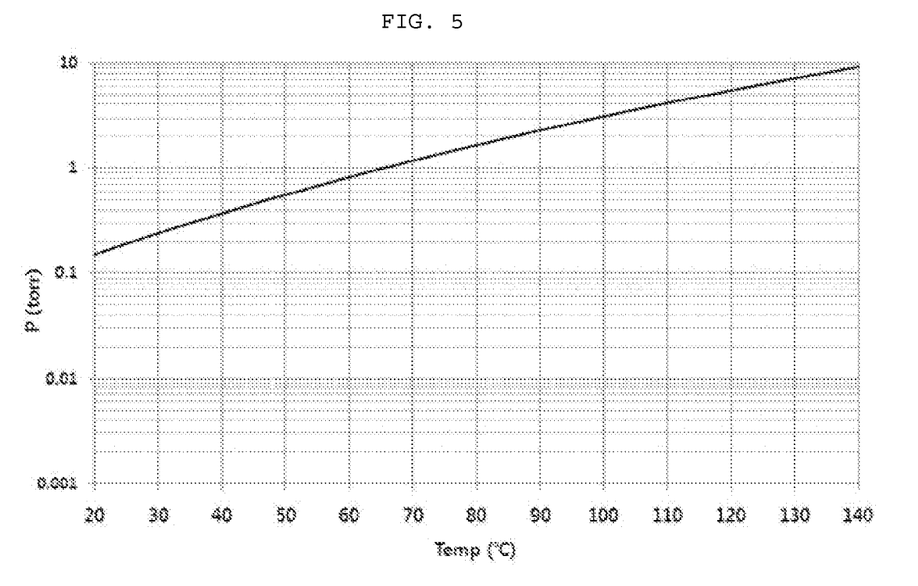
FIG. 5 shows a result obtained by measuring vapor pressure of alkylaminosilane prepared by Example 6.
Figure 6:
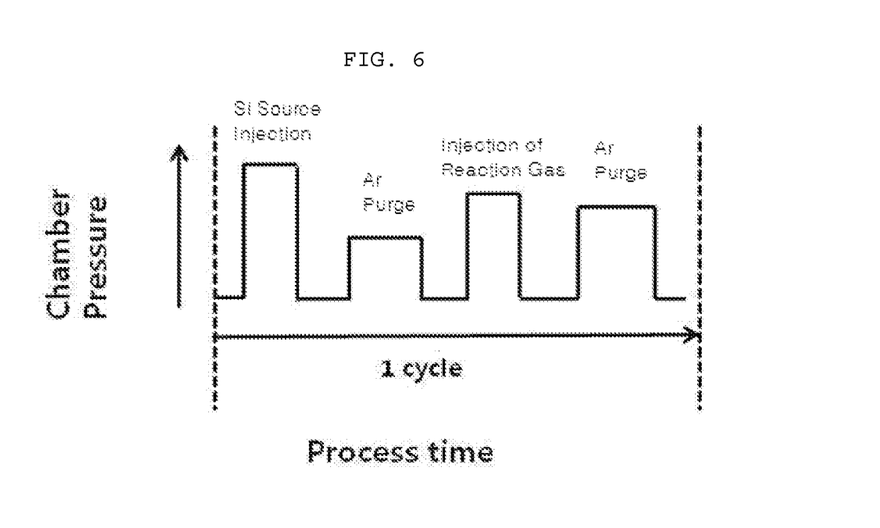
FIG. 6 shows a silicon-containing thin-film deposition method practiced by Examples 7 and 8, and Comparative Example.

Deposition of Silicon Oxide Film by Plasma Enhanced Atomic Layer Deposition (PEALD) Using Amino-Silyl Amine Compound of Present Invention Film forming evaluation was conducted with the amino-silyl amine compounds of Examples 2, 3, and 6 according to the present invention as the composition for forming the silicon oxide film in the general plasma enhanced atomic Layer deposition (PEALD) apparatus using the known PEALD method. Oxygen together with plasma was used as the reaction gas, and argon being an inert gas was used as purge gas. Hereinafter, FIG. 6 and Table 1 specifically show a method for depositing the silicon oxide thin-film.

TABLE 1

| Silicone Oxide Thin-Film Deposition Conditions | | | | | | | | | |
|---|---|---|---|---|---|---|---|---|---|
| Heating | | Time (sec) | Purge | | Oxygen Plasma | | Purge | | |
| Temperature of Precursor (□) | Temperature of Substrate (□) | Required for Injecting Precursor | Flow Rate (sccm) | Time (Sec) | Flow Rate of Oxygen/Argon (sccm) | Time (Sec) | Flow Rate (sccm) | Time (Sec) | Number of Deposition Cycle |
| Bis-Diethylamino Dimethylsilyl Trimethylsilyl Amine | 90 | 100 | 7 | 1100 | 20 | 300/100 | 10 | 1100 | 15 | 50 |

TABLE 1-continued

Silicone Oxide Thin-Film Deposition Conditions

| | Heating | | Time (sec) | Purge | | Oxygen Plasma | | Purge | | |
| --- | --- | --- | --- | --- | --- | --- | --- | --- | --- | --- |
| | Temperature of Precursor (□) | Temperature of Substrate (□) | Required for Injecting Precursor | Flow Rate (sccm) | Time (Sec) | Flow Rate of Oxygen/Argon (sccm) | Time (Sec) | Flow Rate (sccm) | Time (Sec) | Number of Deposition Cycle |
| Tris-Diethylamino Dimethylsilyl Amine | 90 | 100 | 9 | 1100 | 20 | 300/100 | 10 | 1100 | 15 | 50 |
| Tris-Dimethylamino methylsilyl Amine | 75 | 100 | 2.5 | 1100 | 20 | 300/100 | 10 | 1100 | 15 | 50 |

Figure 7:
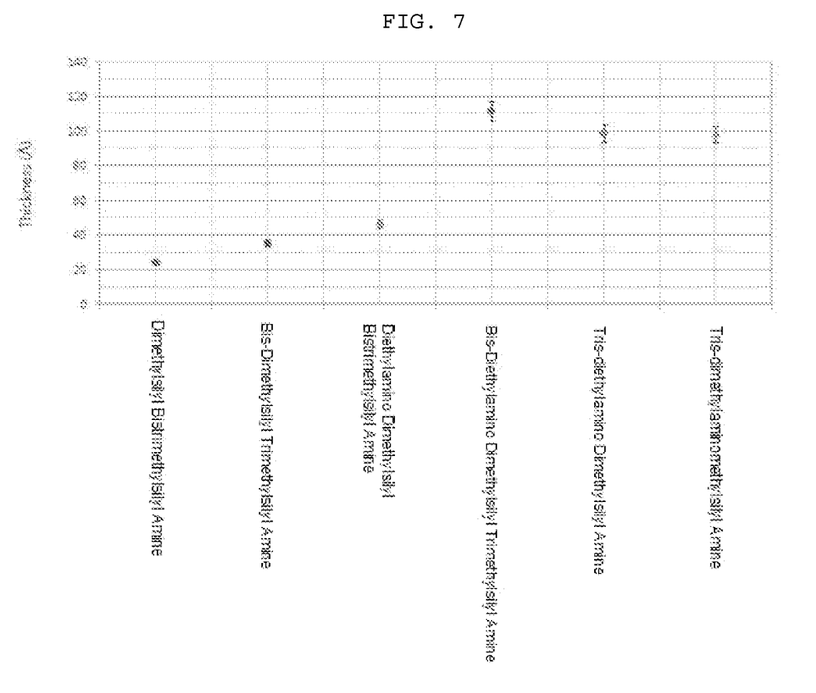
FIG. 7 shows a result showing a thickness of the film by Ellipsometer analysis of the silicon-containing thin-film manufactured by Example 7 and Comparative Example.
Figure 8:
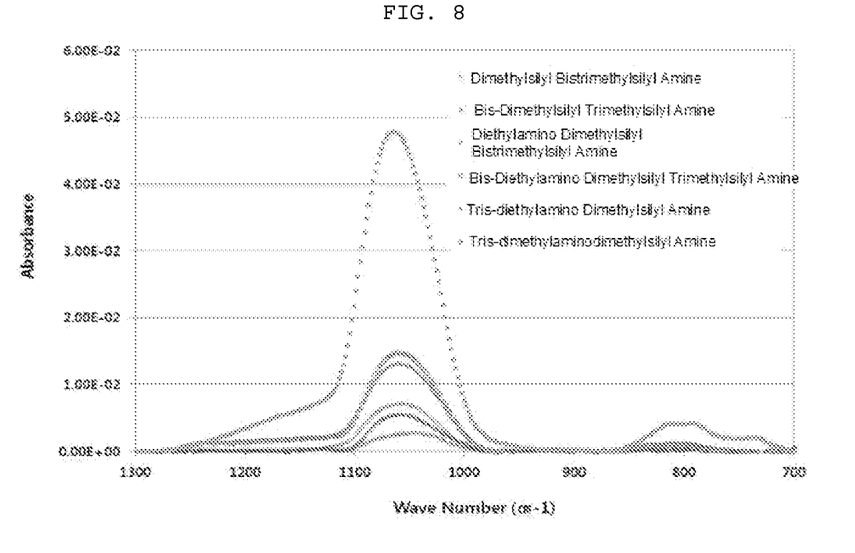
FIG. 8 shows a result obtained by infrared spectroscopy analysis of the deposited silicon-containing thin-film manufactured by Example 7 and Comparative Example.

A thickness of each deposited thin-film was measured by Ellipsometer, and formation of SiO$_2$ thin-film was analyzed by infrared spectroscopy. FIG. 7 shows a thickness of the film by Ellipsometer analysis. It was shown that the thicknesses of thin-films ranging 98 to 112 Å are different from each other depending on the kind or the number of substituents, and it is determined that the thin-film is useful in all silicon oxide thin-film application fields requiring high deposition rate. FIG. 8 shows a result obtained by infrared spectroscopy analysis of the deposited film. It was shown that all of the silicon oxide thin-films were formed, and impurities peak such as C—H, Si—OH was not observed.

That is, it was confirmed that the novel amino-silyl amine compound prepared by the present invention is capable of forming silicon oxide thin-film having high purity and high deposition rate by PEALD, which has high value.

Comparative Example

Deposition of Silicon Oxide Film by Plasma Enhanced Atomic Layer Deposition (PEALD) Using Known Amino-Silyl Amine Compound Film forming evaluation of Comparative Example was conducted by known PEALD under the same deposition conditions as practiced by Example 7 above except for using known amino-silyl amine compound as shown in the following Table 2 instead of using the amino-silyl amine compound of the present invention, and the deposited thin-film was analyzed by the same analysis method and conditions as practiced by Example 7 above and the analysis result thereof was obtained. Hereinafter, FIG. 6 and Table 2 specifically show a method for depositing the silicon oxide thin-film.

It was shown that the thicknesses of thin-films had a range of 21 to 60 Å, having a low deposition rate as compared to the amino-silyl amine compounds of Examples 3, 4 and 6, and all of the silicon oxide thin-films were formed.

TABLE 2

Silicon Oxide Thin-Film Deposition Conditions

| | Heating | | Time (sec) | Purge | | Oxygen Plasma | | Purge | | |
| --- | --- | --- | --- | --- | --- | --- | --- | --- | --- | --- |
| | Temperature of Precursor (□) | Temperature of Substrate (□) | Required for Injecting Precursor | Flow Rate (sccm) | Time (Sec) | Flow Rate of Oxygen/Argon (sccm) | Time (Sec) | Flow Rate (sccm) | Time (Sec) | Number of Deposition Cycle |
| Dimethylsilyl Bistrimethylsilyl Amine | 40 | 100 | 1 | 1100 | 20 | 300/100 | 10 | 1100 | 15 | 50 |
| Bis-Dimethylsilyl Trimethylsilyl Amine | 40 | 100 | 1 | 1100 | 20 | 300/100 | 10 | 1100 | 15 | 50 |
| Diethylamino Dimethylsilyl Bistrimethylsilyl Amine | 80 | 100 | 3 | 1100 | 20 | 300/100 | 10 | 1100 | 15 | 50 |

Example 8

Deposition of Silicon Nitride Film by Plasma Enhanced Atomic Layer Deposition (PEALD) Using Amino-Silyl Amine Compound of Present Invention Film forming evaluation was conducted with the amino-silyl amine compounds of Examples 2, and 4 according to the present invention as the composition for forming the silicon nitride film in the general plasma enhanced atomic Layer deposition (PEALD) apparatus using the known PEALD method. Nitrogen (N$_2$) and ammonia (NH$_3$) together with plasma were used as the reaction gas, and argon being an inert gas was used as purge gas. Hereinafter, FIG. 6 and Table 3 specifically show a method for depositing the silicon nitride thin-film.

TABLE 3

Silicon Nitride Thin-Film Deposition Conditions

| | Heating | | Time (sec) | Purge | | $N_2/NH_3$ Plasma | | Purge | | |
|---|---|---|---|---|---|---|---|---|---|---|
| | Temperature of Precursor (□) | Temperature of Substrate (□) | Required for Injecting Precursor | Flow Rate (sccm) | Time (Sec) | $N_2/NH_3$ Flow Rate (sccm) | Time (Sec) | Flow Rate (sccm) | Time (Sec) | Number of Deposition Cycle |
| Bis-Diethylamino Dimethylsilyl Trimethylsilyl Amine | 90 | 100~400 | 7 | 1100 | 20 | 150/30 | 10 | 1100 | 15 | 50 |
| Tris-diethylamino Dimethylsilyl Amine | 90 | 100~400 | 9 | 1100 | 20 | 150/30 | 10 | 1100 | 15 | 50 |

Figure 9:
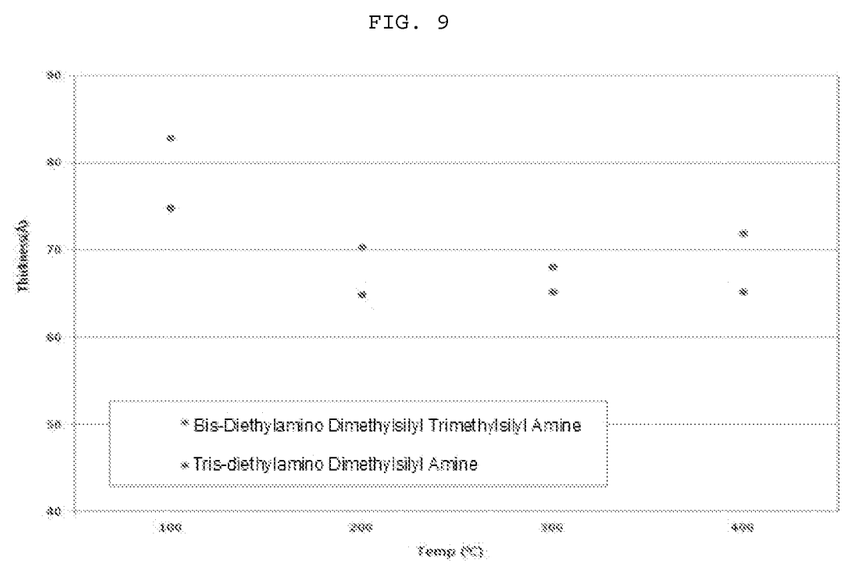
FIG. 9 shows a result showing a thickness of the film by Ellipsometer analysis of the silicon-containing thin-films manufactured by Example 8 and Comparative Example.
Figure 10:
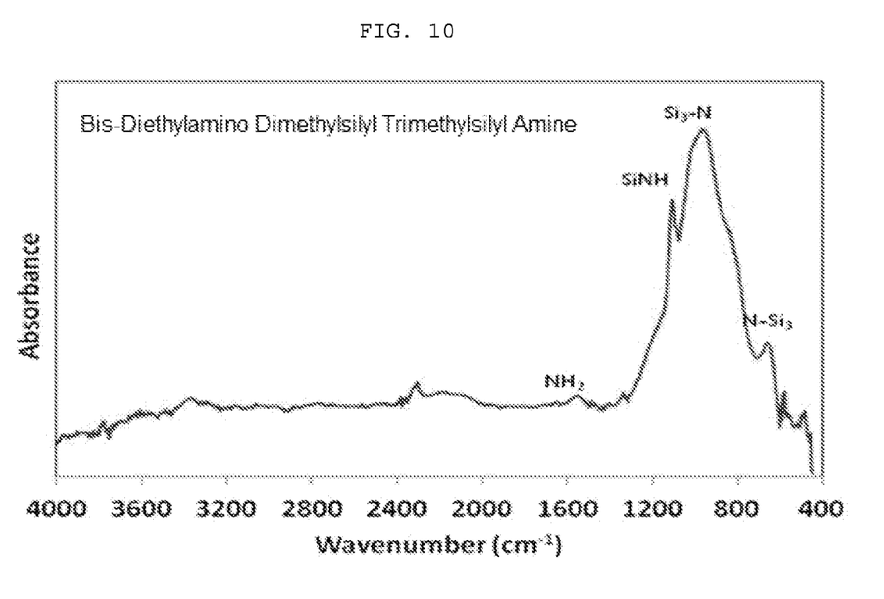
FIG. 10 shows a result obtained by infrared spectroscopy analysis of the deposited silicon-containing thin-film manufactured by Example 8.

A thickness of each deposited thin-film was measured by Ellipsometer, and formation of silicon nitride thin-film was analyzed by infrared spectroscopy. FIG. 9 shows a thickness of the film by Ellipsometer analysis. It was shown that the thicknesses of thin-films ranging 65 to 72 Å are different from each other depending on the kind or the number of substituents, and it is determined that the thin-film is useful in all silicon nitride thin-film application fields. FIG. 10 shows infrared spectroscopy analysis of the deposited thin-film.

That is, it was confirmed that the novel amino-silyl amine compound prepared by the present invention has high value in forming a high purity silicon nitride thin-film capable of being deposited at a low temperature by plasma enhanced chemical vapor deposition (PECVD).

The invention claimed is:

1. An amino-silyl amine compound of Chemical Formula 1:

wherein,

R1 to R4 are each independently hydrogen, halogen, (C1-C7)alkyl, (C2-C7)alkenyl, (C2-C7)alkynyl, (C3-C7)cycloalkyl or (C6-C12)aryl;

R5 to R6 are each independently (C1-C7)alkyl, (C2-C7)alkenyl, (C2-C7)alkynyl, (C3-C10)cycloalkyl or (C6-C12)aryl, or are linked to form 5- to 7-membered alicyclic ring;

R7 to R8 are each independently hydrogen, (C1-C7)alkyl, (C2-C7)alkenyl, (C2-C7)alkynyl, (C3-C10)cycloalkyl or (C6-C12)aryl, or are linked to form 5- to 7-membered alicyclic ring; and the alkyl, alkenyl, alkynyl, cycloalkyl, and aryl of R1 to R4, and the alkyl, alkenyl, alkynyl, cycloalkyl, and aryl of R5 to R8 can further substituted with halogen, (C1-C7)alkyl, (C1-C7)alkoxy, or (C1-C7)aryloxy.

2. The amino-silyl amine compound of claim 1, wherein

R1 to R4 are each independently hydrogen, halogen, (C1-C5)alkyl, (C2-C5)alkenyl, (C2-C5)alkynyl, (C3-C6)cycloalkyl or (C6-C10)aryl;

R5 to R6 are each independently (C1-C5)alkyl, (C2-C5)alkenyl, (C2-C5)alkynyl, (C3-C5)cycloalkyl or (C6-C10)aryl; and R7 to R8 are each independently hydrogen, (C1-C5)alkyl, (C2-C5)alkenyl, (C2-C5)alkynyl, (C3-C5)cycloalkyl or (C6-C10)aryl.

3. The amino-silyl amine compound of claim 2, wherein

R1 to R4 are each independently hydrogen or (C1-C5)alkyl;

R5 to R6 are each independently (C1-C5)alkyl, and

R7 to R8 are each independently hydrogen or (C1-C5)alkyl.

4. The amino-silyl amine compound of claim 1, wherein the Chemical Formula 1 is selected from the following compounds:

-continued

-continued

-continued

-continued

5. The amino-silyl amine compound of claim 1, wherein
R1 to R4 are each independently hydrogen, (C1-C2)alkyl, or (C2)alkenyl;
R5 to R6 are each independently (C1-C3)alkyl or are linked to form a 5-membered alicyclic ring; and
R7 to R8 are each independently hydrogen, (C1-C7)alkyl, (C2-C7)alkenyl, (C2-C7)alkynyl, (C3-C10)cycloalkyl or (C6-C12)aryl, or are linked to form 5- to 7-membered alicyclic ring.

6. The amino-silyl amine compound of claim 1, wherein
R1 to R4 are each independently hydrogen, (C1-C2)alkyl, or (C2)alkenyl;
R5 to R6 are each independently (C1-C3)alkyl or are linked to form a 5-membered alicyclic ring; and
R7 to R8 are each independently hydrogen or (C1-C7) alkyl.

* * * * *